United States Patent [19]

Evans

[11] Patent Number: 5,503,813
[45] Date of Patent: Apr. 2, 1996

[54] MOLYBDENUM RECOVERY FROM EPOXIDATE

[75] Inventor: Thomas I. Evans, Glenmoore, Pa.

[73] Assignee: ARCO Chemical Technology, L.P., Greenville, Del.

[21] Appl. No.: 440,509

[22] Filed: May 12, 1995

[51] Int. Cl.$^6$ .................. C01G 39/00; C07D 301/19; C07D 303/04
[52] U.S. Cl. ................ 423/53; 423/55; 423/58; 423/61; 549/541; 588/223
[58] Field of Search .............. 549/541; 423/53; 588/223

[56] References Cited

U.S. PATENT DOCUMENTS

| | | | |
|---|---|---|---|
| 4,075,277 | 2/1978 | Castagna et al. | 423/53 |
| 4,328,191 | 5/1982 | Su et al. | 423/53 |
| 4,403,572 | 9/1983 | Moore et al. | |
| 4,455,283 | 6/1984 | Sweed | 423/53 |
| 4,485,074 | 11/1984 | Poenisch | 423/53 |
| 5,171,868 | 12/1992 | Albal et al. | |
| 5,276,235 | 1/1994 | Dubner | |
| 5,290,527 | 3/1994 | Marquis et al. | 423/53 |

*Primary Examiner*—Joseph E. Evans
*Attorney, Agent, or Firm*—William C. Long

[57] ABSTRACT

Epoxidate from the molybdenum catalyzed epoxidation of an olefin such as propylene with a hydroperoxide such as ethylbenzene hydroperoxide is treated with 2 to 15 times the stoichiometric equivalent of aqueous base such as sodium hydroxide to form $Na_2MoO_4$ and the resulting mixture is phase separated to separate an organic phase reduced in molybdenum and a net aqueous stream containing removed molybdenum, the mass ratio of the organic phase to the net aqueous stream being 450–3,000/1.

5 Claims, 1 Drawing Sheet

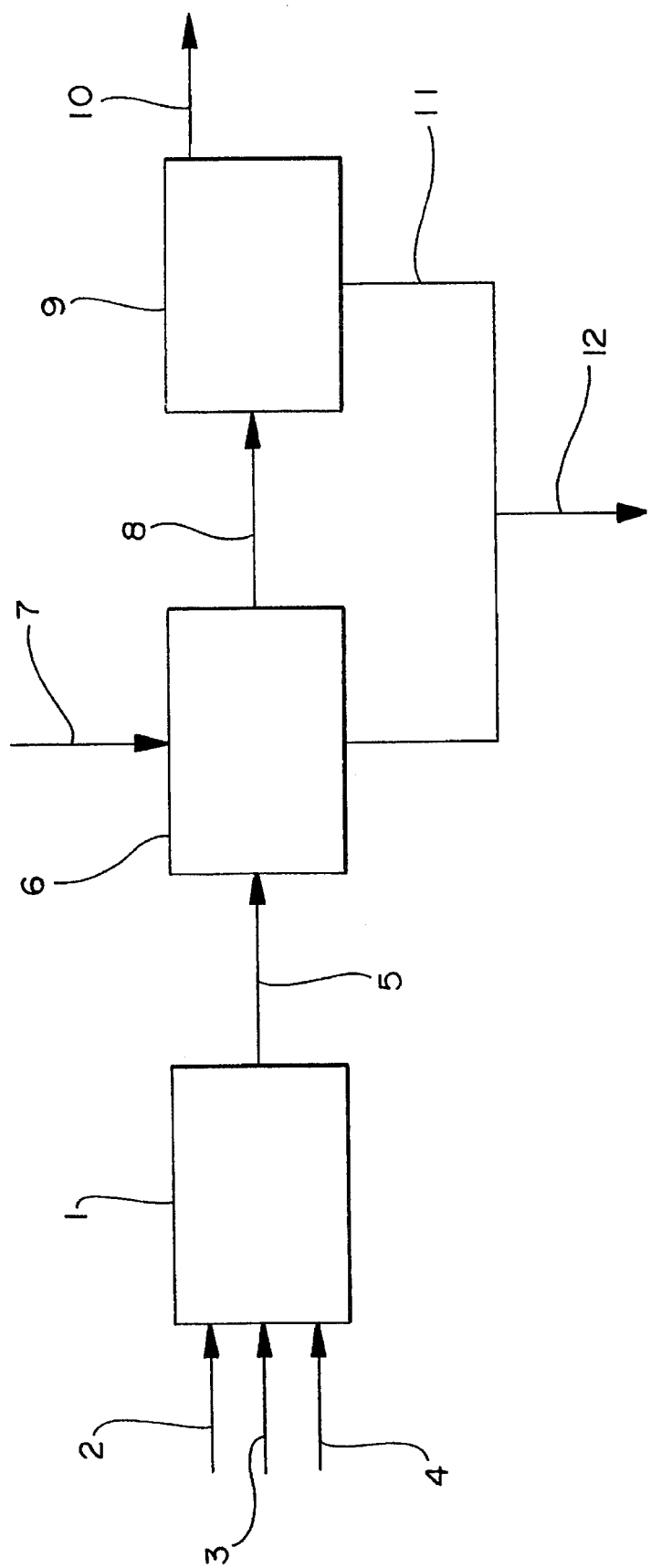

100
MOLYBDENUM RECOVERY FROM EPOXIDATE

FIELD OF THE INVENTION

The present invention relates to an improved method for the separation of molybdenum values from epoxidates which result from the molybdenum catalyzed epoxidation of an olefin such as propylene by reaction with a hydroperoxide such as ethylbenzene hydroperoxide.

DESCRIPTION OF THE PRIOR ART

An extremely successful process for the co-production of propylene oxide and styrene monomer involves the molecular oxygen oxidation of ethyl benzene to from ethyl benzene hydroperoxide, the catalytic reaction of the hydroperoxide with propylene to form propylene oxide and 1-phenyl ethanol, and the dehydration of the 1-phenyl ethanol to styrene monomer. The basic patent describing this process is U.S. Pat. No. 3,351,635.

In practice of the process, the epoxidation reaction mixture, usually after separation of unreacted propylene by distillation, is treated with aqueous caustic in an amount in excess of that necessary both to react with contained molybdenum values to form sodium molybdate and to react with organic impurities such as acids and phenols which are also o contained in the epoxidate. See U.S. Pat. Nos. 4,405,572, 5,276,235, and 5,171,868, for example.

A problem which has existed in such prior practices has been the formation of relatively large quantities of an aqueous process stream containing molybdenum, sodium and organics and the disposal of such aqueous process streams. The presence of molybdenum is particularly troublesome since this material must be removed prior to outfall to satisfy environmental restrictions.

BRIEF DESCRIPTION OF THE INVENTION

In accordance with the present invention, the molybdenum containing epoxidate is given a light, near-stoichiometric treatment with a basic material such as sodium hydroxide or sodium carbonate sufficient to selectively convert a predominance of the contained molybdenum values to sodium molybdate or the equivalent without effecting substantial reaction with organic acids and phenols. Sufficient water is also provided so that the resulting mixture can be phase separated with recovery of a small aqueous phase containing a predominance of the molybdenum values and an organic phase greatly reduced in molybdenum content.

DESCRIPTION OF THE DRAWING

The attached drawing illustrates in schematic form a practice of the invention.

DETAILED DESCRIPTION

Referring to the attached drawing, reaction of an olefin such as propylene with an organic hydroperoxide such as ethylbenzene hydroperoxide takes place in reactor 1 in accordance with known procedures. Olefin is introduced via line 2, hydroperoxide via line 3, and molybdenum catalyst via line 4.

Epoxidate comprised of unreacted olefin, alcohol corresponding to the hydroperoxide, epoxide product, molybdenum catalyst values, and organic impurities such as acids, phenols and the like is removed from zone 1 via line 5 and passes to treatment zone 6. In zone 6, the epoxidate is contacted with aqueous caustic or its equivalent at conditions effective to selectively convert the predominance of the molybdenum catalyst values contained therein to sodium molybdate while leaving the organic impurities present in the epoxidate largely unaffected. The net aqueous caustic or equivalent is introduced into zone 6 via line 7, and a recycle aqueous stream from separator 9 is introduced via line 11.

After thorough mixing in zone 6, the resulting mixture passes via line 8 to decantation zone 9 where the mixture is phase separated. An upper organic phase comprised of the epoxidate organic components and greatly reduced in contained molybdenum values is removed via line 10 while the lower aqueous phase containing the predominance of the molybdenum values in concentrated solution is recycled to zone 6 via line 11 with a purge containing net molybdenum values being removed via line 12. Each of the phases removed from zone 9 can be further treated in accordance with procedures which will be described later herein.

Generally, epoxidate from the olefin/hydroperoxide epoxidation reaction will contain from about 20–60 ppm by weight molybdenum values expressed as Mo. In accordance with the present invention, the net caustic or an equivalent base is introduced into zone 6 via line 7 in amount of about 2 to 15 times the stoichiometric amount needed to convert the molybdenum contained in the epoxidate to $Na_2MoO_4$ or the equivalent where a base other than a sodium compound is used, i.e. $K_2MoO_3$ where a potassium compound is used and $(NH_4)_2 MoO_3$ where an ammonium compound is used. The use of lower amounts of base results in less molybdenum removal while the use of higher amounts of base results in excessive reaction with organic impurities in the epoxidate.

Sufficient water is provided along with the base via line 7 and via recycle from zone 9 to form a distinct aqueous phase in decantation zone 9 with the mass ratio of the organic phase to aqueous phase in zone 9 being illustratively in the range of about 2/1 to 6/1.

The aqueous phase is removed from zone 9 via line 11. A portion is purged via line 12 with the remainder recycled to zone 6 to provide, along with the aqueous base stream added via line 7, sufficient water to achieve good separation in zone 9.

The purge stream removed via line 12 contains the removed molybdenum values, i.e. a predominance of the molybdenum values in the epoxidate reaction mixture. The purge stream also contains sufficient base cation to avoid a build up of base cation in the system. It is important in order to achieve the objectives of the invention that the mass ratio of the treated organic phase removed from zone 9 via line 10 to the purge stream separated via line 12 be quite high, i.e. in the range 450/1 to 3000/1.

Sodium hydroxide is the preferred base used to treat the epoxidate. Other basic materials which might be used include sodium carbonate, potassium hydroxide, potassium carbonate, ammonium hydroxide, ammonium carbonate, and the like.

The basic treatment of the epoxidate is conveniently carried out at temperatures ranging from about 10° to 90° C. although higher temperatures can be employed where higher than atmospheric pressure is maintained.

Through practice of the invention, greater than 80% of molybdenum values are removed from the epoxidate up to 90% or more. Greater than 90% of the molybdenum values can be removed by providing multiple caustic treatment and decantation zones, i.e. additional zones equivalent to zones 6 and 9. Generally, less than 2% (based on carbon) of the organic impurities are separated with the molybdenum in accordance with the invention. An organic backwash, for example with ethylbenzene, of the concentrated molybdenum aqueous stream, purged via line 12, serves to recover dissolved aromatic organics which are later converted to styrene monomer.

While it is preferred to treat the entire epoxidate from zone 1 by the process of the invention, it is quite feasible to first remove unreacted olefin by distillation from the epoxidate prior to treatment in accordance with the invention.

After separation of molybdenum values by the process of the invention, the epoxide containing organic stream can be treated by conventional washing and distillation procedures to separate the various components. Organic impurities can be separated by supplemental caustic treatment, the great advantage being that because the predominance of molybdenum has previously been removed, disposal of subsequent aqueous streams is greatly facilitated.

The concentrated molybdenum aqueous stream removed from zone 9 via line 11 and purged via line 12 can be recovered and sold as such. Alternatively it can be subjected to thermal oxidation to remove contained organics, the recovered solids acidified with HCl or $H_2SO_4$ to drive off carbonates as $CO_2$, and the resulting organic free, carbonate free sodium molybdate solution sold as such. Preferably, the as-is stream or the thermally oxidized, organic free sodium molybdate values can be (1) acidified with hydrochloric acid to precipitate saleable molybdic acid solid, (2) treated with calcium chloride or lime to precipitate saleable calcium molybdate solid, or (3) treated with ferric solutions to precipitate saleable ferric-molybdenum solids.

Solids from all three options must be efficiently separated from solution. Techniques to achieve this separation include conventional filtration, flocculation, and clarification. To make saleable, the cake must be thoroughly dewatered via press filtering and/or hot air drying.

The following example illustrates practice of the invention.

EXAMPLE

Referring to the accompanying drawing, propylene is epoxidized in zone 1 by reaction with ethylbenzene hydroperoxide in the presence of a soluble molybdenum catalyst in accordance with known procedures.

The epoxidation reaction mixture is removed from zone 1 and passed via line 5 to treatment zone 6 at the rate of 500,000 lbs/hr. Composition of the epoxidation mixture by weight is 7% propylene oxide, 50% ethyl benzene, 2% propylene, 30% 1-phenyl ethanol, 0.5% oxygenated organic impurities including acids, phenols, and the like, and 45 ppm molybdenum values as Mo.

In zone 6, the epoxidation reaction mixture is contacted and admixed with an aqueous sodium hydroxide stream introduced via line 7. The aqueous sodium hydroxide stream comprises about 1% by weight NaOH in water and is fed to zone 6 at the rate of 5,700 lbs/hr. Contact conditions in zone 6 comprise 35° C. and 14.7 psig. Also fed to zone 6 is the recycled aqueous phase from decantation zone after separation of the purge stream via line 12. The aqueous phase is recycled to zone 6 in amount of 125,550 lbs/hr.

The admixture from zone 6 passes via line 8 to decantation zone 9 where the admixture is separated into immiscible phases, the upper organic phase containing the organic components of the epoxidation reaction mixture and the lower aqueous phase comprised of an aqueous sodium molybdate solution containing the predominance of the molybdenum values from the epoxidate.

The lower phase comprised by weight of 86% water, 6% $Na_2MoO_4$, and 8% organics is recycled via line 11 to zone 6 with a purge removed via line 12 at the rate of 700 lbs/hr (75 gallons/hr) and passes to an HCl treatment zone wherein it is acidified by contact with aqueous HCl (37% by weight HCl in water) in amount of 35 lbs/hr. Molybdic acid (hydrated $MoO_3$) is recovered by precipitation and filtering in amount of 15–18 lbs. contained Mo per hr. In an advantageous alternative procedure, the stream removed via line 12 is subjected to a thermal oxidation with a hydrocarbon fuel such as methane, illustratively at 1800° F. or so, and solids recovered comprising the molybdenum values.

The upper organic phase containing by weight 0–10 ppm molybdenum as Mo is removed from zone 9 via line 10 at the rate of 505,000 lbs/hr and is treated in a conventional manner for recovery of the various components.

In the above treatment NaOH was added via line 7 in a stoichiometric ratio to molybdenum of 6:1 to form $Na_2MoO_4$. The mass ratio of the organic phase to the aqueous phase in zone 9 was 4:1. As a result of the treatment described 80–90% of the molybdenum values in the epoxidate were separated thus greatly facilitating further treatment of the organic stream and disposal of aqueous streams from such further treatment.

I claim:

1. The method of selectively removing contained molybdenum values from an epoxidate mixture comprised of products of the catalytic epoxidation of an olefin with an organic hydroperoxide which comprises contacting the mixture with an aqueous base, the amount of base being 2 to 15 times the equivalent amount to form a molybdate with the contained molybdenum values, and separating the resulting mixture into an aqueous phase containing the predominance of the molybdenum and an organic phase, separating from the aqueous phase a stream containing the net molybdenum values removed from the epoxidate, the mass ratio of the said organic phase to said stream containing the net molybdenum values being 450–3000/I.

2. The method of claim 1 wherein the olefin is propylene and the hydroperoxide is ethylbenzene hydroperoxide.

3. The method of claim 1 wherein the base is sodium hydroxide.

4. The method of claim 1 wherein the base is sodium carbonate.

5. The method of claim 1 wherein the said stream containing the net molybdenum values is thermally oxidized to remove contained organics.

* * * * *